United States Patent [19]

Dewitt et al.

[11] 3,960,946

[45] June 1, 1976

[54] PROCESS FOR THE MANUFACTURE OF OXALYL DIHYDRAZIDE AND THE USE OF SAME AS A COOLANT IN GAS GENERATING COMPOSITIONS

[75] Inventors: Ivan L. Dewitt; Eugene Pacanowsky, both of Elkton, Md.

[73] Assignee: Thiokol Corporation, Newtown, Pa.

[22] Filed: Sept. 10, 1974

[21] Appl. No.: 504,784

Related U.S. Application Data

[62] Division of Ser. No. 233,790, March 10, 1972, Pat. No. 3,839,105.

[52] U.S. Cl.............................. 260/561 H; 423/407; 149/19.4; 149/19.5; 149/19.9; 149/19.91; 149/36; 149/76; C06B/47/08
[51] Int. Cl.².................. C07C 97/16; C01B 21/16; C06B 45/10
[58] Field of Search..................... 260/561 H, 557 H; 423/407, 410; 149/36

[56] References Cited
UNITED STATES PATENTS

| | | | |
|---|---|---|---|
| 2,615,862 | 10/1952 | McFarlane, Jr. | 260/561 H |
| 3,022,345 | 2/1962 | Szmuszkovicz | 260/561 H |
| 3,061,642 | 10/1962 | Weisse | 260/561 H |
| 3,211,720 | 10/1965 | Heubusch | 260/561 H |
| 3,631,005 | 12/1971 | Fan | 260/561 H |
| 3,787,482 | 1/1974 | Bersworth | 260/561 H |

OTHER PUBLICATIONS

The Chemistry of Hydrazine by Audrieth, p. 214, John Wiley & Sons, New York, copyright 1951.

*Primary Examiner*—Benjamin R. Padgett
*Assistant Examiner*—Donald P. Walsh
*Attorney, Agent, or Firm*—Stanley A. Marcus; Royal E. Bright; Thomas W. Brennan

[57] ABSTRACT

A curable homogeneous gas-generating composition composed essentially of oxalyl dihydrazide coolant combined with: (a) a perchlorate oxidizer selected from the group consisting of ammonium perchlorate, the alkali metal perchlorates, and the alkali earth metal perchlorates, (b) a combustible fuel binder, and (c) propellant adjuvants.

A process for the preparation of oxalyl dihydrazide is also disclosed.

The gas-generating compositions of the present invention have greatly improved combustion characteristics and exhibit reduced flame temperatures.

5 Claims, No Drawings

PROCESS FOR THE MANUFACTURE OF OXALYL DIHYDRAZIDE AND THE USE OF SAME AS A COOLANT IN GAS GENERATING COMPOSITIONS

This is a division of application Ser. No. 233,790 filed Mar. 10, 1972, now U.S. Pat. No. 3,839,105.

BACKGROUND OF THE INVENTION

1. Field of the Invention

This invention relates to a process for the preparation of oxalyl dihydrazide and the use of oxalyl dihydrazide in gas generating compositions. More particularly, this invention concerns the addition of oxalyl dihydrazide to perchlorate-based gas generating compositions to improve their combustion characteristics so that they can be used for such applications as gas turbine and jet engine starters and with proper safety precautions in automobile protective crash bag inflation.

The novel coolant of this invention has the structure

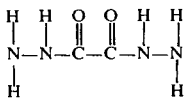

The process for preparation of the above oxalyl dihydrazide material is described below.

2. Description of the Prior Art

Within recent years, especially where applications in the aerospace or aeronautical fields are concerned, there has been an increasing reliance upon the use of devices driven or actuated through the generation of gases. These devices commonly derive their energy from the controlled combustion of solid gas-generating compositions in the gas turbine engines. The combustion of these solid compositions to gaseous products can be used to pressurize a fluid or drive a turbine to produce mechanical or electrical energy or to start various mechanical devices. The gas-generating devices are particularly advantageous in that they are capable of producing a rather substantial amount of power considering the relatively light weight of the fueled gas generator compared to conventional gas or oil powered generators. Because of their high power to low weight ratio, these devices are especially suited to drive gas turbines and jet type engines for intermittant or short term use.

Recently a novel group of coolants has permitted the use of perchlorate oxidizers in gas-generating compositions. These compositions are disclosed in U.S. Pat. Nos. 3,193,421 and 3,214,304. Specifically the above disclosures teach that when energetic perchlorates heretofore unusable as oxidizers in gas-generating compositions are formulated with oxalohydroxamic acid, also referred to as dihydroxyglyoxime (DHG) and related compounds, a substantial decrease in flame temperature is obtained. More recently, dihydroxglyoxime (DHG) and related compounds have been used as coolants in gas-generating compositions containing polynitrated organic or polynitro organic oxidizers replacing the perchlorate oxidizer. These compositions are disclosed in U.S. Pat. No. 3,362,859. It is therein taught that for certain applications where corrosion or erosion problems are critical that perchlorate oxidizers are unsuitable because of the corrosive effects of the hydrogen chloride gas produced during combustion. As a general teaching, this is accurate. However, perchlorate-based gas-generating compositions remain quite useful in applications where corrosion or erosion is not a critical problem. Thus, for example, in many military gas turbine starter applications, the hardware downstream from the starter exhaust is constructed of metal which is highly resistant to corrosion or errosion. In addition, any hydrogen chloride gas produced during combustion of the perchlorate-based gas-generating composition does not normally remain in the gas turbine for a significant period of time since such gas is purged from the system by non-corrosive gases generated by the fuel used to operate the gas turbine.

The perchlorate-based gas-generating compositions of the present invention are useful to a limited degree in applications such as inflatable gas bags because of their relatively low flame temperatures. In this latter application, care is required to design an inflatable bag which is impermeable to hydrogen chloride gas and which is unlikely to rupture during inflation.

Gas-generating compositions useful in the applications to which this invention is directed must meet a number of requirements which are difficult to satisfy. Thus, gas-generating compositions must be ballistically stable after prolonged storage at extreme temperatures ranging from as high as 180°F to as low as −80°F. In addition, particularly for aerospace and military applications, the compositions must be readily ignitable within these same temperature ranges. Furthermore, the compositions must be relatively insensitive to shock, be heterogeneous in content, have substantial elasticity to minimize gaps or voids and burn evenly and consistently. Finally, the oxidizer in gas-generating compositions must have a relatively slow burning rate and burn at relatively low flame temperatures.

The most difficult of these requirements has been the attainment of relatively low flame temperatures. In this context the term relatively low flame temperature is more readily understood by comparison between the flame temperatures of gas-generating compositions and solid rocket propellant compositions. For example, it is well known in the propellant art that propellant compositions have flame temperatures on combustion in the neighborhood of 4000°F to 5000°F or more. Such high flame temperatures are destructive to parts fabricated of commercial metal alloys such as the stainless steels over any sustained period of time. In fact, prolonged exposure to these higher temperatures attack many of the specially formulated so called "heat resistant alloys". However, the erosion and corrosion of the metal missile parts due to the high flame temperatures produced in combustion is of little importance in missiles since they are designed as expendable "one-shot" pieces of hardware. On the other hand, gas-generating compositions used in such applications as starters for gas turbines or jet engines must operate at much lower flame temperatures in order to avoid damage to the gas turbine or jet engine. In these applications, there is a continuing demand for gas-generating compositions with lower flame temperatures. For example, in certain military gas turbine applications, the gas-generating composition must operate at flame temperatures of less than about 2000°F. In other military and commercial gas turbine applications it is anticipated that flame temperature requirements will arise for compositions having flame temperatures of less than 1500°F or perhaps even lower. In comparison with the flame temperatures of propellant compositions (i.e. 4000°F or higher) these are relatively low flame temperatures.

It is evident from the requirements existant in the field of gas-generating compositions that a need exists for gas-generating compositions with flame temperatures lower than those yet achieved in the compositions of the prior art.

Accordingly, it is an object of this invention to prepare novel gas-generating compositions superior in several aspects to compositions of the prior art. It is a further object of this invention to prepare gas-generating compositions which are stable, easily ignitable, and whose combustion is smooth and continuous. It is a still further object of this invention to prepare solid gas-generating compositions which upon combustion produce lower flame temperatures than has been possible with other gas-generating compositions of the prior art. Finally, it is an object of this invention to provide a process for the manufacture of oxalyl dihydrazide.

Other objects will become apparent to those skilled in the art from a consideration of the following detailed description.

SUMMARY OF THE INVENTION

As the result of an extensive investigation, it has been discovered that the objects set forth above can be accomplished by means set forth below.

In practice, a novel and superior gas-generating composition is prepared by mixing, casting, and curing the oxalyl dihydrazide coolant of this invention with (1) an oxidizer (2) a combustible fuel binder with or without (3) propellant adjuvants or conditioning agents.

DESCRIPTION OF THE PREFERRED EMBODIMENTS

One of the essential components of this invention is oxalyl dihydrazide which is used as a coolant to reduce the flame temperature of perchlorate-based gas-generating compositions. Oxalyl dihydrazide is prepared by a one step reaction process involving the addition of diethyloxalate to hydrazine in a solvent. The reaction may be carried out in an ethanol solution or in a distilled water reaction medium. The distilled water reaction medium is especially preferred since it produces much larger yields. Upon addition of diethyloxalate to hydrazine, an immediate and quantitative precipitation of oxalyl dihydrazide results. The precipitate is filtered, washed, and dried to produce a pure product.

Chemical reactions are as follows:

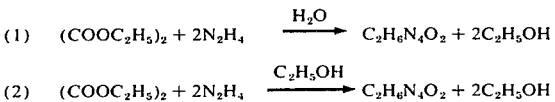

The gas-generating composition of this invention is composed essentially of from about 10 to 60% by weight of oxalyl dihydrazide, preferably above 20% for greater flame temperature reduction, mixed with:

1. From about 20–80% by weight of an inorganic perchlorate oxidizer preferably ammonium perchlorate. However, the alkaline earth metal perchlorates and the alkali metal perchlorates are satisfactory.
2. From about 15–35% by weight of a combustible fuel binder. In general, any of the fuel binders known to be useful in gas generator compositions may be utilized in preparing the present compositions. The fuel binder generally consists of a liquid polymer and one or more curing agents. The liquid polymer forming the basis of the fuel binder may commonly be a liquid polyester particularly a modified polyester such as a carboxyl-terminated linear polyester, a polyester-polyurethane copolymer, and a polyester-polyurethane copolymer terminated with thiol groups. Other telechelic polymers which may advantageously be used are, for example, a carboxyl-terminated linear aliphatic hydrocarbon, a hydroxyl-terminated linear aliphatic hydrocarbon, a polycarbonate, a polyacrylate, a polyurethane, a polyepoxide, a polythiopolymercaptan, a butadiene-acrylic acid copolymer, and a butadiene-acrylonitrile copolymer as well as blends of these polymers.
3. Up to 10% by weight of a propellant adjuvant. The presence of propellant adjuvants while not essential to the operability of the inventive gas-generating compositions are preferably present in order to achieve optimum performance. Where such an adjuvant is used, it will ordinarily comprise between 0.25 to 5% by weight of the gas-generating composition and will seldom comprise more than 10% by weight of the gas-generating composition.

The above components of the gas-generating composition are combined to form a heterogeneous composition, blended thoroughly to produce a uniform mixture, and then cast or extruded and cured using procedures well known in the gas generator art so that they will burn evenly and continuously within the gas generator. Since the final cured gas-generating composition contains several ingredients, it is essential for satisfactory performance that the composition be thoroughly mixed and blended to assure uniformity.

1. Oxidizer

As indicated above, the perchlorate oxidizer, combustible fuel binder, and propellant adjuvants can be varied as to content and choice. For example, numerous perchlorates including the alkaline earth metal perchlorates and the alkali metal perchlorates, the metallic perchlorates generally and ammonium perchlorate can be used as oxidizers. However, ammonium perchlorate is the favored perchlorate oxidizer primarily because it produces more fully gaseous products during combustion than do the other perchlorates. In addition, it is available in large quantities in a high state of purity at low cost.

In general, varying proportions of the oxidizer can be employed in the gas-generating compositions of this invention. For example, depending upon the use intended, the oxidizer can be present in the cured solid gas-generating composition in sufficient quantity so that it makes up about 20 to 80% by weight of the finished compositions.

Compositions containing the lower percentage of oxidizer, in the range of 20 to 50%, have a lower burning rate, low flame temperatures and thus would be useful for gas turbine and jet aircraft starters; whereas the compositions containing the higher percentage (about 50% to 80%) of oxidizer would be useful in preparing gas-generating compositions where a high burning rate is desirable. In all instances, the balance of the gas-generating composition will consist of 10 to 60% by weight of the invention coolant and 15 to 35% by weight of fuel binder with up to 10% by weight of one or more propellant adjuvants if desired.

2. Fuel Binder

The fuel binder referred to throughout this application refers to combustible polymeric resins or their percursors which can be cured to the desired hardness and which are utilized as fuels for the oxidizers. The term "Fuel Binder" as used throughout this invention not only includes the polymeric composition which is present in a major amount but also includes a minor amount of one or more curing agents used in the resin art which imparts the required rigidity or body to the final useable gas-generating composition. Because the curing agent will vary according to the polymer or polymers being treated, the amount and composition of curing agent or agents used will be varied to provide desirable mechanical properties needed to meet each specific application.

The carboxyl-terminated polyesters used as fuel binders in the present compositions may be prepared in known manner by reacting a polycarboxylic acid with a hydroxylated, preferably polyhydroxylated, compound under reaction conditions such as temperature, pressure and catalysts described in the resin art. The reaction product is a liquid carboxyl-terminated prepolymer which is admixed with other components of the composition and cured to form the final gas-generating composition.

Typical polycarboxylic acids which can be used as reactants in preparing the above described carboxyl-terminated polyesters include oxalic, adipic, sebacic, maleic, fumaric, and others as well as mixtures of these acids. Hydroxylated reactants include among others the glycols such as; ethylene glycol, diethylene glycol, propylene glycol, polybutylene and polypropylene glycols, glycerols, sorbitols, castor oil, 1,2,6-hexane triol and the like as well as mixtures of these compounds and their analogues. In the alternative, any of the numerous commercially available polyesters can be used as the source of the fuel binder.

The carboxyl-terminated aliphatic hydrocarbons may be carboxyl-terminated butadiene polymers prepared as described in Berenbaum U.S. Pat. No. 3,235,589 and may have a molecular weight within the range 500 to 10,000.

The hydroxyl-terminated aliphatic hydrocarbons may be hydroxyl-terminated butadiene polymers prepared by ozonizing the butadiene homopolymer and then reducing the ozonized polymer with a metal hydride to form the hydroxyl-terminated polymer in accordance with the procedure described in the patent application to Farr et al, Ser. No. 219,780 filed Aug. 27, 1962 now abandoned. The hydroxyl-terminated butadiene polymer may also be prepared by the process described in Ryan et al. Canadian Patent No. 838,233. Alternatively, a commercially available hydroxyl-terminated butadiene liquid polymer, as for example, the hydroxyl-terminated butadiene polymers designaed R-45M and R-45HT from the Atlantic Richfield Company, may conveniently be used.

Where the binder is to be polyurethane based, the polyurethane can be made by reacting an organic isocyanate or diisocyanate with one or more polyols, polyethers, polyesters, or other hydroxylated materials in the presence of a suitable base such as an amine. Alternatively, the polyurethane can be derived by curing commercially available polymers or their mixtures.

Whereas ordinarily the fuel binders contemplated are a single polymer, such as the polyacrylamides, polyesters, polyurethanes and the like, frequently it is advantageous to prepare mixtures of those resins or the resins modified by imparting additional functional groups to the resinous molecule. For example, a modified polyurethane resin can be prepared by reacting a polyurethane with 1,2-ethane dithiol to result in a prepolymer which can be cured by the polysulfide type of cure. Another approach to the same type of prepolymer is to react a carboxyl-terminated polyester with the 1,2-ethane dithiol.

The liquid polythiolpolymercaptans may be prepared as disclosed in U.S. Pat. No. 2,466,963 and may have molecular weights in the range 1000 to 5000.

In all instances, the resin used as a fuel binder is cured according to the curing techniques well known to the particular resin art using the usual polymerization catalysts, curing agent or accelerators commonly used. For example, the polyesters are cured at temperatures ranging from 80°–180°F. and above, using the usual curing agents such as polyimines, polyepoxides and the like. Similarly, the polyurethane prepolymers can be cured at temperatures varying between ambient and 200°F. and even higher when treated with curing agents such as polyols. The mercaptan-terminated polyurethanes are cured at temperatures ranging from 120°–200°F. using peroxide curing agents such as benzoyl peroxide. The carboxyl-terminated hydrocarbon polymers and acrylobutadiene copolymers such as the acrylic acid-butadiene copolymers can be conveniently cured with polyepoxides, e.g., trifunctional epoxide resins based on p-amino-phenol, aziridines and epoxide azirdines in known manner. Small amounts of curing catalysts of the metal salt type, e.g., iron, chromium, or stannous salts of linoleic or 2-ethyl hexanoic acid may be used in conjunction with the polyepoxide curing agent.

The hydroxyl-terminated hydrocarbon polymers can be cured in a one-step process by reacting the hydroxyl-terminated polymer with an organic isocyanate or diisocyanate or in a two step process by first reacting the hydroxyl-terminated hydrocarbon polymer with an organic isocyanate or diisocyanate to form a urethane prepolymer and then reacting the resulting isocyanante-terminated prepolymer with a diol or an aamine. In the fuel binder of the present invention, the one-step curing process is preferred. These procedures are described in detail in an article by P. W. Ryan appearing in the British Polymer Journal Volume 3, May, 1971 pages 145–153.

The liquid polythiolpolymercaptans can be cured with various oxidizing agents as disclosed in U.S. Pat. No. 2,466,963.

Since the methods of preparing or modifying the various resins used as binders are not the novel feature of this invention no attempt is made to describe these manipulations in detail. It shall suffice to say that the preparative methods and curing techniques are well known procedures described in the technical literature particularly in the "Plastics Application Series" published by Reinhold Publishing Corporation, New York City, N.Y.

3. Propellant Adjuvants

In addition to the curing agents, solvent, polymerization and vulcanization catalysts and the like which are described separately and included within the fuel binder content of the inventive gas-generating compositions, certain conditioning or modifying agents can often be advantageously added to gas-generating compositions to alter or improve their physical and combustion characteristics. For convenience, these substances are herein generically referred to as propellant adjuvants and they can be present in the finished gas-generating composition in amounts from up to about 10 parts by weight down to 0 part by weight of the final gas-generating composition.

More commonly, however, the adjuvants comprise from about 0.25 parts by weight or even less up to about 5 parts by weight of the gas-generating composition. Among the many propellant adjuvants which can be used are included the following typical materials: darkening agents such as carbon black or lamp black, ballistic agents such as ferrocene, hygroscopicity inhibitors such as magnesium oxide, and high temperatures stabilizers such as 2,4-diamino-6phenyltriazine (DAPT), and various combustion catalysts. The combustion catalysts are of diverse structure but generally are compounds containing oxygen. They include, among many others, oxides, such as magnesium, iron, copper, titanium, calcium, molybdenum, and vanadium oxides and the like. Especially effective as combustion catalysts are the chromates and dichromates, generally with ammonium dichromate being a preferred catalyst. Other satisfactory combustion catalysts include barbituric acid, sodium barbiturate, metallo organics such as iron and cobalt dicyclopentadienyl, and ferric and colbalt acetyl acetonate and certain dyes including copper phthalocyanine.

4. Compounding the Ingredients

In preparing the solid gas-generating composition the following procedure among many others can be used.

The dried oxidizer such as a perchlorate (20–80 parts by weight) is reduced to a finely divided condition by grinding or some other means. From about 10–60 parts by weight of oxalyl dihydrazide and from about 15–35 parts by weight of combustible fuel binder, either prepared earlier from the reactants, or as the commercially available monomer or polymer is placed in a blending vessel equipped with an efficient spark proof mixer and the fine particles of the oxidizer are added thereto.

Also added at this time are 0–10 parts by weight of any propellant adjuvants that are required. During these additions efficient mixing is maintained until a homogeneous mixture results. The total mixing time necessary for a uniform mixture varies according to the batch size but ordinarily at least 30 minutes of mixing is required with 90 minutes or more representing the extreme time. Finally the curing agent or agents where necessary are added and the mixing continued for an additional ½ to 1 hour. Finally the uniformally blended uncured gas-generating composition is cast into a gas generator engine and the composition is cured at the required temperature until the desired hardness is obtained. The curing times and temperatures are dependent upon the particular resin used as a binder, and the batch size among other things and thus cannot be stated with precision. However, the following ranges of time and temperature are typical for curing gas generating compositions containing the fuel binders described below.

| Binder | Range of curing Temperatures, °F. | Range of curing Time, hours |
|---|---|---|
| Polyester | 80–180 | 6–50 |
| Polyurethane | 80–200 | 6–70 |
| Polysulfide | 120–200 | 6–70 |
| Polybutadiene | 80–200 | 6–70 |

In order to illustrate the preparation and use of the novel gas generating compositions of this invention, the following examples are submitted.

EXAMPLE 1

Preparation of Oxalyl Dihydrazide Using Ethanol As The Reaction Medium

A solution of diethyloxalate in ethanol was produced by dissolving 365 grams of diethyloxalate in 14 liters of ethanol at room temperature. 160.2 grams of anhydrous hydrazine was then added dropwise to the ethanolic solution of diethyloxalate with stirring. A quantitative and immediate precipitation of material occurred.

The precipitated material was then recrystallized yielding three distinctly different crystalline forms. A colorless monoclinic needle with an exceptionally high length to diameter ratio is the predominating form but large well formed cubic crystals can also be seen. The third form is best described as a slightly yellow hexagonal crystal. Formation of this type takes place from a point source and radiates in all possible directions to form a well regulated star shaped pattern. Each of these crystals can be handpicked from a mixture to yield uncontaminated samples for identification.

Differential thermal analysis of each type crystal showed no differences. An endotherm starting at 237°C is interrupted by an exotherm at 249°C which is resolved into maxima at 261 and 266°C. These thermal excursions are accompanied by a weight less ranging from 37 to 49 percent of the original sample weight.

Elemental analyses of each of the three crystal forms gave similar results with excellent agreement with theory.

| Crystal Form | Analyses |
|---|---|
| Monoclinic | $C_2H_{6.02}N_{3.99}O_{2.00}$ |
| Cubic | $C_2H_{5.96}N_{3.96}O_{2.01}$ |
| Hexagonal | $C_2H_{5.92}N_{3.98}O_{2.00}$ |
| Oxalyl dihydrazide theoretical formula = $C_2H_6N_4O_2$ | |

EXAMPLE 2

Preparation of Oxalyl Dihydrazide Using Distilled Water As The Reaction Medium using a 1.5 liter breaker, 100 grams of hydrazine hydrate (1 mole) was placed in 500 ml of distilled water and warmed to 40°C. Addition of diethyloxalate (73 grams, 0.5 mole) was conducted over a 45 minute period to maintain the temperature of 45°–50°C. The suspension of product was still capable of being stirred. These same amount of reactants were added in a total of eight successive increments until eight moles of hydrazine and four moles of diethyloxalate were added. At this point, the system was no longer capable of being stirred efficiently. The ethanol produced in the reaction and the water of hydration from the hydrazine contributed to the total liquid volume. After setting overnight, a total volume of 1150 ml was noted with approximately 550 ml of solid layer. The liquor was dark yellow-orange. This material was filtered yielding 700 cc of liquor and after washing twice with 300 ml of water each time resulted in 700 grams of wet cake. The wet cake was dried and yielded 534 grams (92.2 percent theory) of very finely divided needle crystals. This material was examined by infra red spectroscopy and differential thermal analysis and found to be equivalent to the oxalyl dihydrazide made by the process described in Example 1. The quantity of oxalyl dihydrazide produced by this process constitutes a 10 fold improvement in yield per gallon over the yield obtained by the process disclosed in example 1. Elemental analysis of the product was shown to be representative of $C_{2.00}H_{6.00}N_{4.02}O_{2.00}$ as compared to the theoretical formula $C_2H_6N_4O_2$.

The material produced by this process was then added to three liters of water at 90°F and cooled overnight to recrystallize it. The product was dried at 105°C and yielded 417 grams (88.3 percent theory). This indicates a solubility loss of 6 grams per liter. Analysis of this material showed an empirical formula of $C_{2.00}H_{5.96}N_{4.02}O_{2.00}$.

Three additional batches of oxalyl dihydrazide were prepared by adding 730 grams of diethyloxalate (5 mole) to 500 grams of hydrazine hydrate (10 mole) in 750 ml of water while maintaining a maximum temperature of 50°C. The resulting product was recrystallized by the same technique as the test batch above and yielded 2345 grams (96.2 percent theory).

The oxalyl dihydrazide produced in the above manner had a decomposition point of 244°C and a density of 1.62 g/cc.

EXAMPLES 3 and 4

Gas Generating Compositions Containing Oxalyl Dihydrazide As A Coolant

The combustible fuel binder used in this embodiment is a carboxyl-terminated polyester resin prepared by condensing adipic acid with diethylene glycol in known manner. Alternatively, a carboxyl-terminated polyester containing 37.5% oxygen may be purchased commercially as, for example, the carboxyl-terminated polyester referred to as HX-730 sold by Minnesota Mining and Manufacturing Company or as F 1747 sold by Witco.

To a suitable blending vessel fitted with a vertical planetary mixer is added 25.0 parts by weight of the above polyester, 1.0 parts by weight of carbon black, 1.0 parts by weight of 2,4-diamino-6-phenyl-triazine(-DAPT) a high temperature stabilizer, and 25.0 parts by weight of oxalyl dihydrazide. These components are mixed for 10 minutes, then 48.5 parts by weight of ammonium perchlorate oxidizer are added and the resultant blend mixed for an additional 30 minutes. At the end of this time, a curing system comprising 1.42 parts by weight of tris[1-(2-methyl) aziridinyl] phosphine oxide and 2.10 parts by weight of 1,1'-(sulfonyldiethylene) bis-2-methyl-aziridine is added and the mixture stirred for an additional 20 minutes. The flame temperature of the combustion is determined by casting a representative sample of the gas generating composition in a gas generator and curing at 150°F for 96 hours.

A second composition is prepared using the same procedure described above except that a standard coolant material dihydroxyglyoxime (DHC) is used in place of the oxalyl dihydrazide coolant.

The flame temperature of the composition containing the inventive oxalyl dihydrazide coolant was 1906°F compared to a flame temperature of about 2100°F for the gas generating composition containing the standard DHG coolant material.

EXAMPLES 5–10

Preparation of Gas Generating Compositions Using Greater And Lesser Quantities of Oxalyl Dihydrazide In these examples, the formulations were prepared substantially as disclosed in Example 1.

In order to measure the effect of varying quantities of oxalyl dihydrazide on the flame temperature of the gas generating composition, the oxalyl dihydrazide was increased in increments as shown below while decreasing the ammonium perchlorate oxidizer correspondingly. The same polyester binder was used as in Examples 1 and 2 and the amount of binder was held constant at 20 parts by weight of the total composition. The adjuvants in the compositions are the same as in Examples 1 & 2.

| Example No. Components | 5 | 6 | 7 | 8 | 9 | 10 |
|---|---|---|---|---|---|---|
| Polyester fuel binder | 20 | 20 | 20 | 20 | 20 | 20 |
| Ammonium perchlorate | 60 | 55 | 50 | 45 | 40 | 30 |
| Oxalyl dihydrazide | 20 | 25 | 30 | 35 | 40 | 50 |
| Flame Temperature (°F) | 2953 | 2535 | 2139 | 1876 | 1756 | 1628 |
| Solids in exhaust | 0.0 | 0.0 | 1.8 | 3.8 | 5.7 | 9.3 |

EXAMPLES 11–16

Preparation of Gas Generating Compositions Containing Varying Quantities of Oxalyl Dihydrazide And An Increased Amount of Polyester Binder In these examples, the formulations were prepared substantially as described in Example 1. In order to measure the effect of oxalyl dihydrazide coolant on the flame temperature of gas generating compositions containing higher amounts of polyester binder, the polyester binder of Example 1 was increased to 30 parts by weight of the total composition and the oxalyl dihydrazide varied in quantity in the same manner as in Examples 3–8.

The results were as follows:

| Example No. Components | Weight Percent | | | | | |
|---|---|---|---|---|---|---|
| | 11 | 12 | 13 | 14 | 15 | 16 |
| Polyester fuel binder | 30 | 30 | 30 | 30 | 30 | 30 |
| Ammonium perchlorate | 50 | 45 | 40 | 35 | 30 | 20 |
| Oxalyl dihydrazide | 20 | 25 | 40 | 35 | 40 | 50 |
| Flame Temperature (°F) | 1848 | 1749 | 1688 | 1646 | 1603 | 1506 |
| Solids in Exhaust | 5.2 | 7.2 | 9.2 | 11.0 | 12.6 | 15.3 |

We claim:

1. A process for the preparation of oxalyl dihydrazide which comprises reacting diethyloxalate and hydrazine at a temperature between about 30°C and about 70°C in a medium consisting substantially of distilled water.

2. A process as defined in claim 1 wherein the temperature is from about 40°C to about 60°C.

3. A process as defined in claim 2 wherein hydrazine hydrate is the source of the hydrazine in the reaction mixture.

4. In a method for making oxalyl dihydrazide wherein a dialkyl oxalate is reacted with hydrazine in a solvent medium, the improvement comprising conducting said reaction in a substantially distilled water solvent medium.

5. The improved method of claim 4 wherein diethyloxalate is reacted with hydrazine at a temperature of from about 40°C to about 60°C.

* * * * *